United States Patent
Charles

(10) Patent No.: US 7,627,488 B1
(45) Date of Patent: Dec. 1, 2009

(54) METHOD TO IMPROVE HOSPITAL REVENUES

(76) Inventor: Ronald Alan Charles, 8906 Wallington Dr., Houston, TX (US) 77096

( * ) Notice: Subject to any disclaimer, the term of this patent is extended or adjusted under 35 U.S.C. 154(b) by 1103 days.

(21) Appl. No.: 10/863,678

(22) Filed: Jun. 8, 2004

Related U.S. Application Data

(60) Provisional application No. 60/492,477, filed on Aug. 4, 2003.

(51) Int. Cl.
*G06Q 10/00* (2006.01)
*G06Q 50/00* (2006.01)

(52) U.S. Cl. ........................................ 705/2

(58) Field of Classification Search .................. None
See application file for complete search history.

(56) References Cited

U.S. PATENT DOCUMENTS

| | | | | |
|---|---|---|---|---|
| 6,345,260 | B1* | 2/2002 | Cummings et al. | 705/8 |
| 2002/0010597 | A1* | 1/2002 | Mayer et al. | 705/2 |
| 2002/0019749 | A1* | 2/2002 | Becker et al. | 705/2 |
| 2002/0026328 | A1* | 2/2002 | Westerkamp et al. | 705/2 |
| 2002/0032580 | A1* | 3/2002 | Hopkins | 705/2 |
| 2002/0042724 | A1* | 4/2002 | Victor | 705/2 |
| 2002/0062224 | A1* | 5/2002 | Thorsen et al. | 705/2 |
| 2002/0103680 | A1* | 8/2002 | Newman | 705/4 |
| 2003/0050794 | A1* | 3/2003 | Keck | 705/2 |
| 2003/0208380 | A1* | 11/2003 | Honeycutt | 705/2 |
| 2004/0078220 | A1* | 4/2004 | Jackson | 705/2 |
| 2004/0220829 | A1* | 11/2004 | Baharav et al. | 705/2 |

* cited by examiner

*Primary Examiner*—Gerald J. O'Connor
*Assistant Examiner*—Sheetal R Rangrej
(74) *Attorney, Agent, or Firm*—Buskop Law Group, PC; Wendy Buskop

(57) ABSTRACT

A method for improving hospital revenues by creating a special care unit entails providing a connection site for a qualified patient who is the member of an association to request an actual time to be seen by a team member within a special care unit in a hospital. The request for the actual time to be seen by the team member is confirmed and the qualified patient is evaluated by the team member at the special care unit within thirty minutes of the actual time to ascertain a medical problem. The method continues by treating the qualified patient based on an evaluation of the medical problem and discharging the qualified patient. A marketing agreement with the association is created, wherein the association markets the special care unit to the members. The association is registered the with the special care unit to identify other members as qualified patients.

14 Claims, 1 Drawing Sheet

METHOD TO IMPROVE HOSPITAL REVENUES

The present application claims priority to co-pending U.S. Provisional Patent Application Ser. No. 60/492,477 filed on Aug. 4, 2003.

FIELD

The present embodiments relate to methods for improving hospital revenues.

While these methods have nearly universal application within varying departmental hospital environments, a number of features of the present embodiments are optimized for use within a hospital's Emergency Department facility.

BACKGROUND

The present embodiments relate generally to a process for managing health care and address many of the problems faced today by those involved with health care: payers, patients, and providers. The methods relate particularly to techniques for improving personalized care at hospitals that interface health plan associations who have decided to seek health care services from a doctor and/or some other type of health care provider. These calls are answered by nurses and/or other types of health care professionals, who use the proprietary information tools and processes of the network management system to help patients assess health needs and then select appropriate care.

The United States ranks first in the world in per-capita health care expenditures. At a time when national health care costs continue to escalate at an alarming rate, managed-care companies and the government have been successful in holding down payments to hospitals; but too often the patient feels unattached from the process. This feeling often leads to a reluctance of patients to seek out the help they need.

Additionally, profit margins of hospitals are decreasing yearly. To survive financially, hospital administrators have been forced to develop novel means of ensuring that their hospital is properly compensated for all services rendered and that patients are treated in manner that encourages them to return to the hospital in times of need. Today, the provision of medical care or personal care for a patient in a hospital often assumes a subordinate role to the extensive amount of information that the hospital requires from the patient. Hospital administrators often need to maintain significant quantities of patient data consisting of information such as admissions, medical history, insurance, and billing. To meet the ever increasing financial demands of providing high quality health care to patient's proper reimbursement from insurance companies is absolutely essential. Complicating the problem is the unique, often hectic, nature of an Emergency Room.

Working under highly stressful conditions, emergency medical team members are routinely forced to forego personalized care in order to balance administrative tasks and treat multiple patients suffering from severe injuries. Often, patients arrive in an Emergency Room with reduced communicative abilities as to their identity, compounded with life threatening injuries that require immediate medical attention. An attending Physician may issue an array of orders ranging from X-rays, administration of medication, and laboratory assays; all of which must be tracked and recorded to insure proper billing and reimbursement. In these situations, it is unacceptable to interfere with the administration of care in order to obtain patient medical care, or resource utilization data. Often when there is interference with the administration of care the patient is ignored as a person and treated as a series of problems. This only adds to anxiety of the patient and increases their feeling of isolation towards the hospital.

A majority of patients initially come to a hospital through the Emergency Room. A patient will inevitably make a decision about using the hospital for future needs, as well as recommending the hospital to others, based on this initial visit and the treatment during that visit. For hospitals to remain viable and competitive, they must make an effort to personalize care in the Emergency Room in order to encourage patients to choose their hospital for future needs.

Furthermore, most patients with insurance obtain their insurance through a membership with an association. Associations can be any group of people from unions to employees of the same company. A need exists for hospitals to implement a marketing agreement with these types of associations. These associations can actively advise their members of the warm and responsive environment in the hospital and the customer friendly atmosphere in the area surrounding the Emergency Room. In return, the hospital would implement a program where a patient belonging to one of these associations would be identified as a qualified patient merely by their membership.

A qualified patient would be identified by uniform, known trademark, employee identification card, or some other means of identification that associates the patient as a member of one the associations. This type of relationship would create revenue for the hospital by increasing the number of people who use the facility and would personalize the experience for the patient.

A need exists for a method to provide emergency health care to patients with insurance. This method would allow hospital administrators to optimize utilization of resources, including utilization of medical personnel, such as nurses, and other medical resources, such as beds, medications, and the like. The method will additionally provide the ability to track effectively the efficiency of patient care provision on a personalized level. This is the ultimate goal of the Emergency Room. In a broader sense, this method would allow hospital administrators to monitor the cumulative activity of a given department over a time period and assess staff and administrative efficiency as needed to determine if personalized care is being given and if those patients are returning to the hospital for their future needs.

SUMMARY

A method for improving hospital revenues begins by creating a special care unit with a connection site for a qualified patient. A qualified patient is the member of an association to request an actual time to be seen by a team member within a special care unit in a hospital. A marketing agreement is established between the special care unit and the association, wherein the association markets the special care unit to the members. The association is registered the with the special care unit to identify other members as qualified patients.

The special care unit establishes an interface to allow qualified patients to request for the actual time to be seen by the team member. The request is confirmed and the qualified patient is evaluated by the team member at the special care unit within thirty minutes of the actual time to ascertain a medical problem. The method ends by treating the qualified patient based on an evaluation of the medical problem and discharging the qualified patient.

BRIEF DESCRIPTION OF THE DRAWINGS

The present embodiments will be explained in greater detail with reference to the appended Figures, in which.

Figure 1:
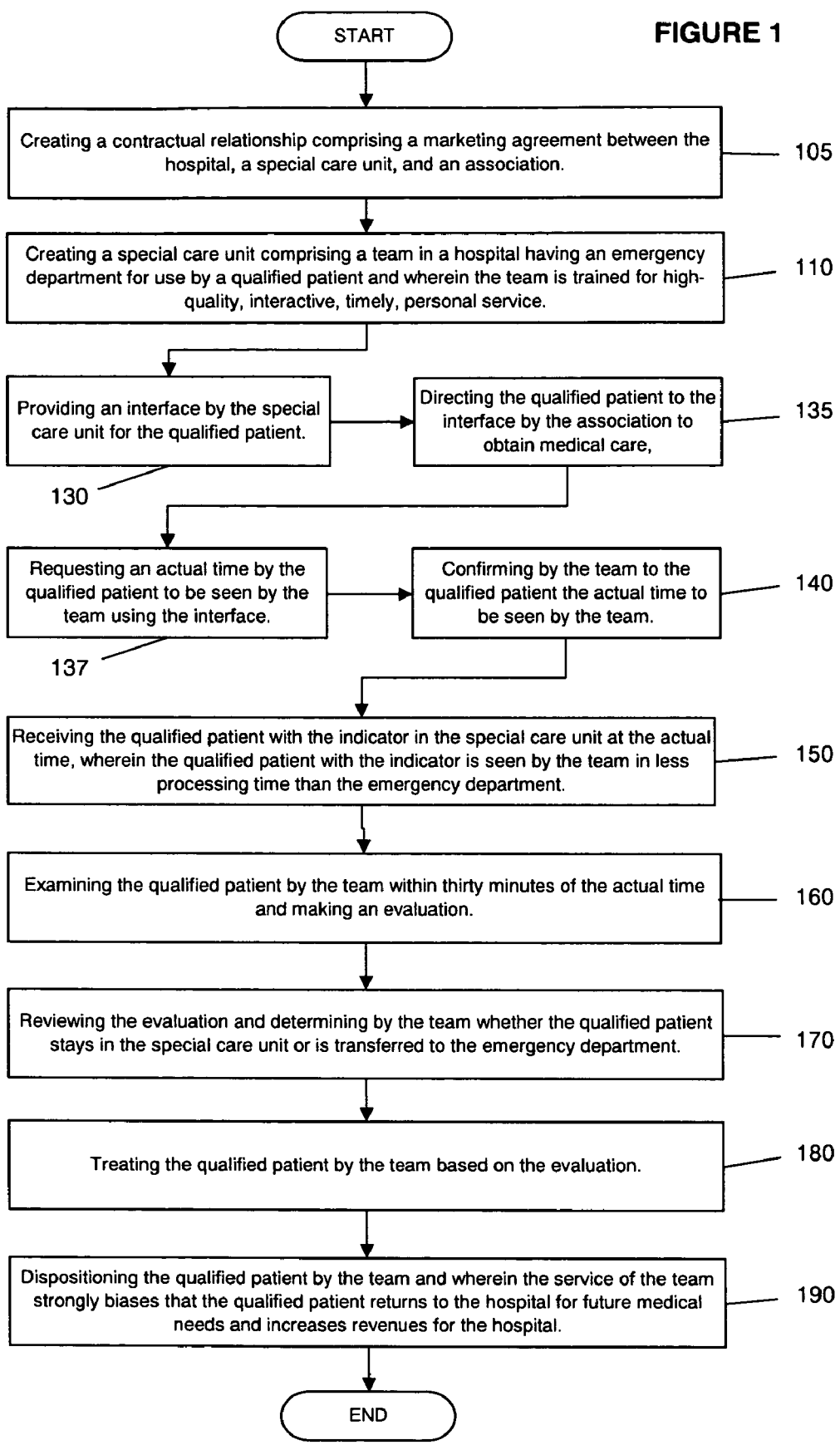
FIG. 1 is a schematic diagram of the steps of an embodiment of a method for improving hospital revenues by creating a special care unit for retaining qualified patients.

The present embodiments are detailed below with reference to the listed Figures.

DETAILED DESCRIPTION OF THE PREFERRED EMBODIMENTS

Before explaining the present embodiments in detail, it is to be understood that the embodiments are not limited to the particular embodiments herein and can be practiced or carried out in various ways.

The embodied methods for improving hospital revenues by creating a special care unit that facilitates the retaining of qualified patients who might not normally come to the hospital establish bonds between patients and the hospital. The established bonds encourage patients to return to the same hospital for future medical needs. The hospital revenues are, therefore, increased due to the return visits. The method is cost effective, saves lives, and increases productivity of workers. The method promotes improves health care. This novel method is designed to get workers back to work quicker, which, in turn, provides an overall stimulus to the economy.

With reference to the Figures, FIG. 1 is a schematic diagram of the steps of an embodiment of the method.

The methods begin by implementing a contractual agreement between the association, hospital, and the management group of the special care unit (105). Under the agreement, the association and the management group work together to market the special care unit to potential qualified patients. The association and the management group notify the potential qualified patients of the locations of the special care units; the hours of available service of the special care units; the phone number of the special care units or a scheduling service; the web site address of the special care units; an information center to answers questions about the special care units; and other pertinent information needed to have the potential qualified patients easily access the special care units.

The method contemplates that the association and the management group accomplish the task of marketing the special care units by newsletters, meetings, e-mail, direct mailings, advertising, and combinations thereof. Examples of advertising include stickers, magnets, promotional items, and other similar tokens used to market the special care units. The associations advise members of the special care units on a regular basis, but at least monthly as a minimum.

The association and the indicator are registered with the special care unit to identify other members as qualified patients. The association attempts to provide appropriate insurance information to the special care unit so the care of the qualified patient can be expedited. The association informs the qualified patient that they should mention the special care unit when they are admitted into the emergency department triage for treatment.

Returning to FIG. 1, the method continues by creating a team for a special care unit (110). The team is made of team members optimally at least three members, a nurse, a physician, and a clerical staff member. This team for the special care unit is trained with a program that focuses on customer service and care. The special care unit team members can have special training, reading materials, tests and evaluations to insure a high level of customer service in the special care unit. The method anticipates that periodic review of the level of care can occur by methods such as comment cards and spot inspections.

Next, as shown in FIG. 1, an interface is provided for a qualified patient to request an actual time to be seen by a team member within the special care unit (130).

The method operates for individuals who are referred to hereafter as qualified patients. Qualified patients are individuals who have contracted for specialized care from a qualified team of health professionals through an organization. Examples of organizations include unions, employers, credit unions, and organizations, such as AAA or AARP.

An organization can be an association of numerous members from a defined region. The method contemplates that the organization incorporates a group of people associated with one another through a health plan.

The qualified patient is a person that can be identified and educated about the special care unit. The special care unit is preferably in a space near or close to the emergency department of a hospital. In the special care unit, the qualified patient's can have the insurance already preprogrammed into a database that enables them to obtain the care from the special care unit.

A qualified patient, as an individual, can be a union member, police officer, hospitality industry member, hospital employee, emergency medical services member, governmental worker, or other workers identified by uniform. The qualified patient can belong to an association, such as a union or a corporation that has a visually identifiably and unique identification mark, such as a sticker with an employee logo, employee badge, distinct trademark, uniform, or a corporation issued smart card.

Family members with insurance are be qualified patients under this method. A family member is a spouse, a dependant, or other specially designated person of the primary insured. Specially designated persons include grandparents, life partners, foster children, dependent aunts, dependent uncles, and siblings.

The qualified patient communicates with the team member using an on-line query service or a telecommunication device. Usable devices include cell phones, satellite phones, or landline phones. The qualified patient can contact the team member using a pager, PDA, or a phone and PDA combination. Other methods include access through an internet website or by mail service. Any one or a combination of these manners to communicate can be used.

Returning to FIG. 1, in creating a special care unit, the qualified patient requests an actual time to be seen by a team member within a special care unit in a hospital having an emergency room or emergency department (130). For example, the actual time requested by the qualified patient is a defined specific time, such as 9:15 am. The qualified patient can request any hour of the day that is not already requested by another qualified patient and during that the special care unit is open. Typically, the special care unit can be open for 10 to 12 hour shifts and possibly for 24/7 shifts (24 hours, 7 days a week). The team member is preferably seen within a 30 minute window around the actual specific time by the qualified patient. If the qualified patient misses this preferred 30 minute window, the methods may include an optional increase in the amount of the co-pay by an amount of a penalty. For example, a penalty of up to $40 can be assessed against a late arriving or non-arriving patient.

The method contemplates that the team member is a person qualified to handle the needs of the qualified patient. Preferably, the team member is a nurse, nurse practitioner, physician, physician assistant, and combinations thereof. Additionally a team member can include a clerical member, trained to handle accounting, billing or other clerical tasks, nurse, nurse practitioner, or other such person in a position to be of qualified assistance.

Under the contractual relationship between the hospital, special care unit, and association, the association directs the qualified patient to the interface in order to schedule an appointment to obtain medical care (135). The qualified patient requests an actual time to be seen by the team (137).

Continuing with FIG. 1, the next step in the methods is providing a confirmation to the qualified patient of the request for the actual time to be seen by the team member (140). The confirmation of the request for the actual time to be seen by the team member can be completed by a verbal confirmation, e-mail confirmation, confirmation by pager, confirmation by written letter (that is faxed), and combinations thereof. Any of the communication methods used by the qualified patient to communicate with the team member can be used by the team member to confirm the request for the scheduled actual time.

Next, the qualified patient with the indicator is received in the special care unit at the actual time (150). The qualified patient with the indicator is seen by the team in less processing time if they were to go through the emergency department.

The process continues by the team the qualified patient team within thirty minutes of the actual time to ascertain a medical problem and make an evaluation (160). The evaluation involves a physical examination, taking of the patient's history and ordering any necessary tests.

The method contemplates that bedside registration for the qualified patient is possible when there available services.

The method continues by the team members reviewing the qualified patient and determining whether the patient stays in the special care unit or is transferred to the emergency department (170). If the qualified patient stays in the special care unit or is transferred to the hospital's emergency room or department the treatment for the qualified patient is based on the special care units evaluation of the medical problem (180). The team member can contact the emergency department and advise of the need to transfer the patient to the emergency department. The patient can then be physically moved to the higher level of care area in the emergency department from the special team unit.

If transfer is not required, then treatment of the qualified patient can include writing a prescription and contacting a contracted pharmacy for expedited filling of the prescription for patient pickup.

Treating of the qualified patient can include ordering a test, such as a blood test, urine test, radiological test, cardiac test, stool test, and combinations thereof. The method contemplates that any test and treating procedures normal to emergency rooms can be used with this method.

The contracted pharmacy can be a 24 hour pharmacy that is near the special care unit. This pharmacy can have a separate contract with trained pharmacists who are adept to quickly filling prescriptions and have the filled prescriptions available to the qualified patient when they arrive at the pharmacy. The contracted pharmacy can have not only increased volume, but increase revenue due to this specially contracted service. The expedited filling of the prescription for patient pickup can be completed by written, electronic, or verbal communication.

One of the goals of this method is to provide good customer service from valet to reserved parking to personalized care to expedite pharmacy prescription pick-up.

Returning to FIG. 1, the final step is dispositioning the qualified patient (190). Dispositioning means discharging from the hospital, transferring the hospital to another area of the hospital, and transferring the patient to a clinic, a nursing home, an assisted-care unit, or to another facility for testing. After the patient is dispositioned, the qualified patient can arrange a follow-up appointment with another physician on the insurance plan in the hospital system, in the same manner as the original appointment was made.

If necessary, and if permitted by the qualified patient, the team member provides the qualified patient's employer or a second physician with treatment information.

The method contemplates that the physician or other team member can use a cell phone with camera system, such as the ones made by Sony or Ericsson, or a digital camera, to photograph and e-mail the patient conditions and situation to a private physician, such as showing the physician an abscess.

The team members can use PDA or personal digital assistants with wireless connectivity in order to access the Internet to register a patient, and enter information while in the examining room directly to the medical records database interfaced and accessed by the team.

Tablet PC's can be used by the team members to draw important information about the condition of the patient. Other types of usable electronic devices include voice recognition, special phone services or template medical record systems.

The team member is part of a qualified team. The qualified team is developed for use in a designated hospital, especially hospitals with emergency rooms. The team operates in an area near or adjacent to the emergency room. These areas are known as "Special Care Units". The "Special Care Units" are designed to allow the qualified team to handle the qualified patients without the need for minimal emergency room equipment. In a preferred embodiment, the special care unit comprises of at least one examination room, at least one computer, and at least one work area; however the special care units can operate with just one examination room. Software on the computer allow for scheduling of qualified patients, production of reports for patient charts, and an interface with hospital and other medical databases to download patient histories. The scheduling software provides an indication of the availability of when a patient can be seen by the team.

The methods contemplate that all information on the patient, the evaluation, and the diagnosis can be completed by using electronic charting, electronic time slotting, and electronic reporting. These types of electronic programs are widely known throughout the medical industry. An example of such as electronic system is the T-System, which is a form of a template medical records system available for use on a laptop or tablet or PDA.

The examining rooms in the "Special Care Units" are typical rooms, with an otoscope, opthalmoscope, thermometer, instruments to take blood pressure, gynecologic equipment, examining tables, chairs, sinks, other tables, scalpels, and medical supplies, such as needles, gauze, and suture material. The methods contemplate that these "Special Care Units" can have the routine equipment and supplies usually stocked in a typical medical care room. The examining rooms include certain medications including pain medications and antiseptics for cleaning wounds. The work area provides an area where paperwork can be handled and where the computer and an Internet connection can be located.

The qualified team typically has at least three members: a clerk, a nurse, and a physician. The team can have more than three members, such as two or more doctors and nurses and/or more clerks depending on the need at a given hospital.

While these embodiments have been described with emphasis on the preferred embodiments, it should be understood that within the scope of the appended claims the embodiments might be practiced other than as specifically described herein.

What is claimed is:

1. A computer implemented method for improving hospital revenues by creating a special care unit for retaining qualified patients, wherein the computer implemented method comprises the steps of
   a. procuring by a computer implemented method an indicator to become a qualified patient; wherein the indicator is selected from the group comprising a uniform, an association identification badge, an association trademark, a sticker with a unique identification mark, a corporation issued smart card, or combinations thereof, from a association wherein the indicator enables care to be provided within thirty minutes of an actual time;
   b. establishing a special care unit comprising at least one examination room, at least one interface to a computer with data storage and computer instructions executable on a computer in the data storage for scheduling actual times to be seen and computer instructions executable on a computer for accessing and downloading patient histories, and computer instructions executable on a computer for production of reports, at least one work area, and forming a team in a hospital having an emergency department for use by the qualified patient, wherein the team has a doctor and at least one member selected from the group comprising: a nurse, a clerk or combinations thereof; further wherein the special care unit provides services including:
      i. providing scheduling services for scheduling the actual time for an examination,
      ii. providing the examination,
      iii. providing at least one test with results enabling the doctor to provide an evaluation,
      iv. providing treatment based on the evaluation; and
      v. providing dispositioning of the qualified patient;
   c. providing the interface for the qualified patients, wherein the interface is selected from the group comprising a website, telephone service, telephone operator, pager, and combinations thereof;
   wherein the interface provides the qualified patient with a communication tool to request the actual time to be seen by the team;
   d. confirming by a computer to the qualified patients the actual time to be seen by the team; and providing a confirmation by a verbal confirmation, an email confirmation, a confirmation by pager, and combinations thereof;
   e. receiving the qualified patients with the indicator in the special care unit at the actual time;
   f. examining the qualified patient by the team within thirty minutes of the actual time;
   g. making the evaluation to either keep the qualified patient in the special care unit or to transfer the qualified patient to a higher level of care area of the emergency department; and
   h. in the special care unit, if no transfer to the higher level of care area is made, then treating the qualified patient by the team.

2. The computer implemented method of claim 1, wherein a qualified patient is a member selected from the group consisting of a union member, police officer, hospitality industry member, teacher, hospital employee, emergency medical services member, a governmental worker, and combinations thereof.

3. The computer implemented method of claim 1, wherein the qualified patient can also be a family member of the qualified patient.

4. The computer implemented method of claim 3, wherein the family member is a member selected from the group consisting of a spouse, at least one dependent, a specially designated person, and combinations thereof.

5. The computer implemented method of claim 1, wherein an association provides the qualified patient with the indicator, and wherein the association comprises at least one of consisting of a union, government agency, emergency medical service group, police officer group, fire fighter group, employee group, human resource department of a company, teacher association, a retired person association, and combinations thereof.

6. The computer implemented method of claim 1, wherein the team further comprises at least a second clerk, at least a second nurse, at least one nurse practitioner, at least a second doctor, at least one physician's assistant, and combinations thereof.

7. The computer implemented method of claim 1, further using a pharmacy to fill prescriptions to have the prescriptions filled when the qualified patient arrives at the pharmacy.

8. The computer implemented method of claim 1, wherein the test is selected from the group consisting of a blood test, urine test, radiological test, cardiac test, stool tests, and combinations thereof.

9. The computer implemented method of claim 1, further comprising the step of arranging a follow-up appointment by the team.

10. The computer implemented method of claim 1, further comprising the step of providing an association with treatment information at the request of the qualified patient and wherein the treatment information is provided by the team.

11. The computer implemented method of claim 1, further comprising the step of providing a second physician with treatment information at the request of the qualified patient and wherein the treatment information is provided by the team member and wherein the providing of the treatment information in an expedited manner enables the hospital to retain the qualified patients and increase hospital revenues.

12. The computer implemented method of claim 1, wherein a marketing agreement is implemented by an association advising the qualified patient about the special care unit by a method selected from a group comprising: sending newsletters, holding meetings, sending e-mail, sending direct mailings, advertising, and combinations thereof.

13. The computer implemented method of claim 12, wherein the advising by the association is implemented on at least a monthly basis.

14. The computer implemented method of claim 12, wherein the advising by the association further comprises providing the qualified patient with locations of the special care unit, availability of the special care unit, a phone number of the special care unit, a web site address of the special care unit, an information center to answers questions about the special care unit; and combinations thereof.

* * * * *